United States Patent
Ächtner et al.

(10) Patent No.: US 9,622,948 B2
(45) Date of Patent: Apr. 18, 2017

(54) PROCESS FOR MANUFACTURING AN EMULSION

(71) Applicant: KAO GERMANY GMBH, Darmstadt (DE)

(72) Inventors: Anja Ächtner, Mannheim (DE); Carsten Häckl, Darmstadt (DE); Jonathan Wood, Weinheim (DE)

(73) Assignee: KAO GERMANY GMBH, Darmstadt (DE)

( * ) Notice: Subject to any disclaimer, the term of this patent is extended or adjusted under 35 U.S.C. 154(b) by 63 days.

(21) Appl. No.: 14/898,563

(22) PCT Filed: Dec. 13, 2013

(86) PCT No.: PCT/EP2013/076474
§ 371 (c)(1),
(2) Date: Dec. 15, 2015

(87) PCT Pub. No.: WO2015/180737
PCT Pub. Date: Dec. 3, 2015

(65) Prior Publication Data
US 2016/0120772 A1    May 5, 2016

(30) Foreign Application Priority Data

Dec. 20, 2012 (EP) .................................. 12198710

(51) Int. Cl.

| | |
|---|---|
| A61K 8/06 | (2006.01) |
| A61K 8/31 | (2006.01) |
| A61K 8/34 | (2006.01) |
| A61K 8/37 | (2006.01) |
| A61K 8/41 | (2006.01) |
| A61K 8/44 | (2006.01) |
| A61K 8/46 | (2006.01) |
| A61Q 5/08 | (2006.01) |
| A61Q 5/10 | (2006.01) |
| A61Q 19/00 | (2006.01) |
| A61K 8/86 | (2006.01) |
| A61K 8/92 | (2006.01) |
| B01F 17/00 | (2006.01) |
| B01F 3/08 | (2006.01) |

(52) U.S. Cl.
CPC ............... *A61K 8/06* (2013.01); *A61K 8/062* (2013.01); *A61K 8/31* (2013.01); *A61K 8/342* (2013.01); *A61K 8/37* (2013.01); *A61K 8/416* (2013.01); *A61K 8/44* (2013.01); *A61K 8/463* (2013.01); *A61K 8/466* (2013.01); *A61K 8/86* (2013.01); *A61K 8/92* (2013.01); *A61K 8/922* (2013.01); *A61Q 5/08* (2013.01); *A61Q 5/10* (2013.01); *A61Q 19/00* (2013.01); *B01F 3/0811* (2013.01); *B01F 17/0042* (2013.01); *A61K 2800/43* (2013.01); *A61K 2800/591* (2013.01); *A61K 2800/805* (2013.01); *A61K 2800/882* (2013.01)

(58) Field of Classification Search
CPC . A61Q 5/10; A61K 8/37; A61K 8/416; A61K 8/44; A61K 8/463; A61K 8/86; A61K 8/922; A61K 8/062; A61K 8/466; A61K 8/06; A61K 8/342; A61K 2800/43; A61K 2800/882; A61K 2800/591; B01F 3/0811
See application file for complete search history.

(56) References Cited

U.S. PATENT DOCUMENTS

| | | | |
|---|---|---|---|
| 8,889,110 B2 | 11/2014 | Braida-Valerio et al. | |
| 2008/0019934 A1* | 1/2008 | Samain | A61K 8/06 424/70.11 |
| 2009/0185994 A1* | 7/2009 | Bistram | A61K 8/39 424/70.11 |
| 2011/0038901 A1 | 2/2011 | Windhab et al. | |

FOREIGN PATENT DOCUMENTS

| | | |
|---|---|---|
| DE | 10 2004 040735 A1 | 3/2006 |
| EP | 2 198 923 A2 | 6/2010 |
| WO | 2011/138348 A1 | 11/2011 |

OTHER PUBLICATIONS

STIC Search Report dated Apr. 28, 2016.*
International Search Report and Written Opinion of the ISA dated Sep. 29, 2015, mailed Oct. 20, 2015.

* cited by examiner

*Primary Examiner* — Eisa Elhilo
(74) *Attorney, Agent, or Firm* — Norris McLaughlin & Marcus PA

(57) ABSTRACT

Present invention relates to a process for manufacturing emulsion composition which comprises an oil phase dispersed in a continuous water phase which is stabilized with a surfactant as an emulsifier. The present invention is on a method for producing an emulsion comprising one or more fatty alcohol, one or more oil liquid at 20° C. and one or more surfactant wherein one or more surfactant is added to the dispersion of one or more fatty alcohol and one or more oil liquid at 20° C. in water at a temperature of 50° C. or higher, preferably 60° C. or higher with the condition that the temperature of the dispersion is at least 10° C. higher than the melting point of fatty alcohol having the highest melting point, more preferably between 60 and 85° C. wherein the emulsion thus obtained does not comprise dispersed droplets with a volume size larger than or equal to 10 μm measured directly without dilution of the emulsion at 20° C. measured with a laser particle size analyzer suitable therefore.

20 Claims, No Drawings

PROCESS FOR MANUFACTURING AN EMULSION

This application is a §371 U.S. National stage of PCT International Patent Application No. PCT/EP2013/076474, filed Dec. 13, 2013, which claims foreign priority benefit of European Patent Application No. EP 12198710.1, filed Dec. 20, 2012, the disclosures of each of which patent applications are incorporated herein by reference.

Present invention relates to a process for manufacturing an emulsion composition which comprises an oil phase dispersed in a continuous water phase which is stabilized with a surfactant as an emulsifier.

Emulsion type of compositions has found their application in various areas. Among them the application in cosmetic products is one major area. Emulsions having either water or oil as a continuous outer phase are manufactured in various ways. One of the common techniques is preparing water and oil phases separately at high temperature, combining them under high shear stress, cooling down the mixture to ambient temperature and adding the remaining ingredients to the emulsion thus obtained.

It has however been observed that manufacturing process affects the appearance of the emulsion in a higher extent. The same composition may have the appearance of an unattractive turbid composition when manufactured with an inappropriate method, but may also have a cosmetic caring shiny emulsion appearance when manufactured according to an appropriate way. The present invention provides a method for manufacturing an emulsion composition in particular an emulsion with water phase as a continuous outer phase which is also called O/W emulsion.

The inventors of the present invention have unexpectedly and surprisingly found that when an emulsion, in particular O/W emulsion, is produced by adding the emulgator into the dispersion of oil phase in water at a high temperature, a creamy, shiny and homogeneous composition is obtained, which has particularly small dispersed droplets.

Accordingly, the first object of the present invention is a method for producing an emulsion comprising one or more fatty alcohol, one or more oil liquid at 20° C. and one or more surfactant wherein one or more surfactant is added to the dispersion of one or more fatty alcohol and one or more oil liquid at 20° C. in water at a temperature of 50° C. or higher, preferably 60° C. or higher, with the condition that the temperature of the dispersion is at least 10° C. higher than the melting point of fatty alcohol having the highest melting point, more preferably between 60 and 85° C. wherein the emulsion thus obtained does not comprise dispersed droplets with a volume size larger than or equal to 10 μm measured directly without dilution of the emulsion at 20° C. measured with a laser particle size analyzer suitable therefore.

The second object of the present invention is the use of the emulsion manufactured according to the method of present invention as a cosmetic composition especially hair cosmetic composition.

The third object of the present invention is a kit comprising two or more compositions wherein one of the compositions is an emulsion manufactured in accordance with the method of present invention.

The fourth object of the present invention is a process for treating hair wherein the emulsion composition manufactured according to the process of the present invention is mixed with another composition and applied onto hair and after leaving on hair for a period 1 to 45 min rinsed off from hair.

Volume droplet size is measured with commercially available equipment available from the company Sequip using laser technology without prior dilution of the emulsion. Emulsion volume droplet size is preferably smaller than or equal to 7.5 μm and more preferably smaller than or equal to 5 μm.

The temperature at which one or more fatty alcohol is melted and one or more oil liquid at 20° C. dispersed is more preferably between 50 and 85° C., most preferably between 60 and 80° C. and in particular between 65 and 75° C.

The emulsion compositions produced in accordance with the present invention comprises one or more fatty alcohols in accordance with the general structure

$R_1$—OH wherein $R_1$ is a saturated or unsaturated, straight or branched alkyl chain having 12 to 30 C atoms which may also be substituted with one or more OH groups, preferably they are selected from fatty alcohols which are solid at 20° C.

The non-limiting examples to suitable fatty alcohols are arachidyl alcohol, behenyl alcohol, *brassica* alcohol, C9-11 alcohols, C10-16 alcohols, C12-13 alcohols, C12-15 alcohols, C12-16 alcohols, C14-15 alcohols, C14-22 alcohols, C20-22 alcohols, caprylyl alcohol, cetearyl alcohol, cetyl alcohol, coconut alcohol, decyl alcohol, hydrogenated *brassica* alcohol, hydrogenated jojoba alcohol, hydrogenated rapeseed alcohol, hydrogenated tallow alcohol, hydroxystearyl alcohol, jojoba alcohol, lauryl alcohol, myristyl alcohol, oleyl alcohol, olive alcohol, palm alcohol, palm kernel alcohol, stearyl alcohol, tallow alcohol, and tridecyl alcohol and their mixtures.

Preferred are cetyl, stearyl, behenyl and cetearyl alcohols and their mixtures. The most preferred is cetearyl alcohol which is the mixture of cetyl and stearyl alcohols.

One or more fatty alcohol is present in the compositions produced in accordance with the method of the present invention at a total concentration 1 to 20%, preferably 1 to 15% more preferably 1 to 10% and most preferably 1 to 5% by weight calculated to the total of the composition.

The emulsion of the present invention comprises one or more oil liquid at 20° C. One or more oil is suitably selected from synthetic and natural oils. Synthetic oils are silicones especially those of nonvolatile ones such as dimethicones with viscosity of 50 to 350 cSt measured by capillary viscosimeter and at 20° C., fatty acid fatty alcohol esters according to the general structure

$R_2C(O)R_3$ wherein $R_2$ is a straight or branched, saturated or unsaturated alkyl with 11 to 21 C atomes and $R_3$ is a straight or branched, saturated or unsaturated alkyl with 1 to 22 C atomes such as behenyl behenate, behenyl isostearte, butyl stearate, butyl oleate, butyl myristate, butyloctyl oleate, cetyl palm itate, cetyl myristate, cetyl oleate, cetyl caprylate, cetyl caprate, decyl oleate, decyl cocoate, decyl isostearate, ethylhexyl myristate, ethyl hexyl laurate, ethyl hexyl oleate, ethyl isostearte, ethyl laurate, ethyl linoleate, ethyl myristate, ethyl oleate, ethyl palm itate, ethylricinoleate, ethyl stearate, hexyl isostearate, hexyl laurate, hexyl myristate, hexyl stearate, hexyl decyl oleate, isobutyl laurate, isobutyl myristate, isobutyl palm itate, isobutyl stearate, isocetyl behenate, isobutyl laurate, isobutyl oleate, isobutyl stearate, isobutyl cocoate, isohexyl caprate, isopropyl palm itate, isopropyl stearate, isopropyl behenate, isopropyl laurate, isopropyl oleate, isopropyl ricinoleate and isopropyl palm itate, and fatty alcohol ethers according to general structure

$R_4OR_5$ wherein $R_3$ and $R_4$ are same or different, straight or branched, saturated or unsaturated alkyl with 8 to 22 C atoms such as dicetyl ether, dimyristyl ether, dicyprylyl ether and dodecyl ether.

Natural oils are mineral oil and plant derived oils such as avocado oil, olive oil, almond oil, peach oil, *passiflora* oil, black cumin oil, borage oils, evening primrose oil, grapeseed oil, hempseed oil, kukui nut oil, rosehip oil, safflower oil, walnut oil and weatgerm oil. The most preferred is mineral oil.

Concentration of oil in the emulsions of the present invention is in the range of 1 to 20%, preferably 1 to 15% more preferably 1 to 10% and most preferably 1 to 5% by weight calculated to the total of the composition.

The emulsions produced in accordance with the method of the present invention comprise one or more fatty alcohols and one or more oil liquid at room temperature.

Preferably the one or more fatty alcohols and one or more oils are comprised at a weight ratio of one or more fatty alcohols to one or more oils less than or equal to 1.

The emulsions produced in accordance with the method of the present invention comprise emulsifying surfactants also referred to as emulgators. Suitable emulgators are anionic, cationic and nonionic ones and preferred are anionic and cationic surfactants and the most preferred are anionic surfactants.

It has also been found that the emulsions manufactured in accordance with the present invention do not require high concentration of emulsifying surfactants and therefore, in accordance with the preferred embodiment of the present invention the weight ratio of total surfactant concentration to total concentration of one or more fatty alcohols and one or more oils, is less than or equal to 0.25, more preferably less than or equal to 0.2, most preferably less than or equal to 0.15 and in particular less than or equal to 0.1.

Total concentration of the surfactants varies in the range of 0.05% to 10%, preferably 0.075 to 7.5%, more preferably 0.1 to 5 and most preferably 0.2% to 2.5% by weight, calculated to total composition.

Non-limiting suitable anionic surfactants are especially the known alkyl sulphates and alkyl ether sulfates, carboxylic acids, in particular in form of their alkali salts, as well as protein fatty acid condensates, fatty acid salts, alkyl/alkenyl succinates, anionic amino acid surfactants especially glutamates such as sodium lauroyl glutamate. The preferred anionic surfactants are alkyl sulphates and alkyl ether sulphates and the most preferred is alkyl sulfate types and their salts such as ammonium C12-15 alkyl sulphate, ammonium C12-16 alkyl sulphate, ammonium coco sulphate, ammonium lauryl sulphate, ammonium myristyl sulphate, magnesium coco sulphate, magnesium lauryl sulphate, magnesium coco/TEA sulphate, MEA lauryl sulphate, MIPA lauryl sulphate, potassium lauryl sulphate, sodium caprylyl sulphate, sodium cetearyl sulphate, sodium cetyl sulphate, sodium coco sulphate, sodium decyl sulphate, sodium ethylhexyl sulphate, sodium lauryl sulphate, sodium myristyl sulphate, sodium oleyl sulphate, sodium stearyl sulphate, sodium tridecyl sulphate, TEA coco sulphate, TEA lauryl sulphate, TEA oleyl sulphate and TIPA lauryl sulphate and their mixtures. Particularly preferred is sodium lauryl sulphate.

Suitable nonionic surfactants are in particular fatty alcohol polyglycol ethers according to general structure

$R_1(OCH_2CH_2)_nOH$ $R_1$ is same as above and n is a number between 1 and 50, preferably 5 and 50, and more preferably 10 and 40 and most preferably 10 and 30.

Suitable non-limiting examples to non-ionic surfactants of fatty alcohol polyglycol ethers are ceteth-1, ceteth-2, ceteth-3, ceteth-4, ceteth-5, ceteth-6, ceteth-7, ceteth-10, ceteth-12, ceteth-13, ceteth-14, ceteth-15, ceteth-16, ceteth-17, ceteth-18, ceteth-18, ceteth-20, ceteth-23, ceteth-24, ceteth-25, ceteth-30, ceteth-40, ceteth-45, isoceteth-5, isoceteth-7, isoceteth-10, isoceteth-12, isoceteth-15, isoceteth-20, isoceteth-25, isoceteth-30, isosteareth-2, isosteareth-3, isosteareth-5, isosteareth-8, isosteareth-10, isosteareth-12, isosteareth-15, isosteareth-18, isosteareth-20, isosteareth-22, isosteareth-25, isosteareth-50, steareth-1, steareth-2, steareth-3, steareth-4, steareth-5, steareth-6, steareth-7, steareth-8, steareth-10, steareth-11, steareth-12, steareth-13, steareth-14, steareth-15, steareth-16, steareth-20, steareth-21, steareth-25, steareth-27, steareth-30, steareth-40, steareth-50, ceteareth-2, ceteareth-2, ceteareth-2, ceteareth-2, ceteareth-2, ceteareth-2, ceteareth-2, ceteareth-3, ceteareth-4, ceteareth-5, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, beheneth-2, beheneth-5, beheneth-10, beheneth-15, beheneth-20, beheneth-25, beheneth-30, oleth-2, oleth-3, oleth-4, oleth-5, oleth-6, oleth-7, oleth-8, oleth-9, oleth-10, oleth-11, oleth-12, oleth-15, oleth-16, oleth-20, oleth-23, oleth-24, oleth-25, oleth-30, oleth-35, oleth-40, oleth-44, oleth-45 and oleth-50 and their mixtures.

Further suitable non-ionic surfactants are fatty acid alkanolamides, amineoxides, and especially $C_8$-$C_{18}$-alkyl polyglucosides of the general structure

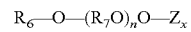
$R_6$—O—$(R_7O)_n$O—$Z_x$ wherein $R_6$ is an alkyl group with 8 to 18 carbon atoms, $R_7$ is an ethylene or propylene group, Z is a saccharide group with 5 to 6 carbon atoms, n is a number from 0 to 10 and x is a number between 1 and 5. Examples are decyl polyglucoside and cocoyl polyglucoside, both being commercially available.

Cationic surfactants especially mono alkyl quaternary ammonium salts of the following general structure

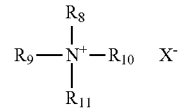

where $R_8$ is a saturated or unsaturated, branched or non-branched alkyl chain with 8-22 C atoms or

$R_{12}CONH(CH_2)_n$ where $R_{12}$ is saturated or unsaturated, branched or non-branched alkyl chain with 7-21 C atoms and n has typical value of 1-4 or

$R_{13}COO(CH_2)_n$ where $R_{13}$ is saturated or unsaturated, branched or non-branched alkyl chain with 7-21 C atoms and n has typical value of 1-4, and and $R_9$, $R_{10}$ and $R_{11}$ are independent from each other H or lower alkyl chain with 1 to 4 carbon atoms, and X is an anion such as chloride, bromide or methosulfate.

Suitable non-limiting examples are cetrimonium chloride, steartrimonium chloride and behentrimonium chloride.

Emulsion of the present invention has a pH in the range of 2 to 11. pH value must be selected in accordance with the particular application of the emulsions.

For example in case the emulsion comprises an oxidizing agent such as hydrogen peroxide then the pH value is acidic and especially in the range of 2 to 5, particularly in the range of 2 to 4. Accordingly emulsions of the present invention can suitable be used as an oxidizing composition and therefore can comprise at least one oxidizing agent, preferably selected from hydrogen peroxide, urea peroxide, melamine peroxide and sodium bromate and most preferably it is hydrogen peroxide preferably at a concentration of 1 to 20%, preferably 1 to 15% and more preferably 2 to 12% by weight calculated to the total of the composition, and has a pH in the range of 2 to 5, preferably 2 to 4.

The emulsions of the present invention can comprises one or more polyol at a concentration in the range of 0.1 to 10%, preferably 0.5 to 7.5%, more preferably 0.75 to 5% and most preferably 1 to 5% by weight calculated to the total of the composition. The term polyol means any compound having 2 or more hydroxyl groups in its molecule. Suitable non-limiting examples are glycerin, 1,2-propylene glycol, polyglycerins with 2 to 10 glycerin units, panthenol, glycol, butyleneglycol, 1,2-butanediol, 1,4, butanediol, 2,3-butanediol, pentylene glycol and 1,5-pentanediol. Preferred are glycerin, 1,2-propylene glycol, glycol, butyleneglycol 1,2-butanediol, 1,4, butanediol, 2,3-butanediol, and panthenol. More preferred are glycerin, 1,2-propylene glycol, glycol, butyleneglycol, and panthenol. Most preferred are glycerine, 1,2-propylene glycol, and panthenol and particularly preferred polyol is glycerin.

The emulsions of the present invention can comprise one or more hair dye or may suitably be mixed with a composition comprising one or more hair dye.

Suitable direct dyes are selected from cationic, anionic, neutral nitro dyes and their mixtures. Preferred are cationic and neutral nitro dyes and their mixtures.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 10% by weight, preferably 0.01 to 7.5% more preferably 0.05 to 5%, most preferably 0.1 to 3% by weight calculated to total composition.

The emulsion composition can comprise additionally or only oxidative dye precursors and an alkalizing agent.

Suitable examples to the oxidative dye precursors are p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxypyridine, 2,6-dimethyl amino-5-aminopyridine, 2-di(hydroxyethyl)amino-5-aminopyridine, 2-hydroxyethyl amino-5-aminopyridine, 4-hydroxy-2,5,6-triaminopyrimidine and/or the water-soluble salts thereof.

Further, Indole and indoline derivatives can as well be contained in the colouring composition of the present invention. Examples to those are: 6-aminoindol, 6-hydroxyindole, 1-ethyl-6-hydroxyindole, 1-methyl-4-hydroxyindol, 1-methyl-6-hydroxyindole, 2-methyl-6-hydroxyindole, 5-hydroxyindol, 4-hydroxyindol, 5,6-dihydroxyindole, 6-aminoindoline, 6-hydroxyindoline, 1-ethyl-6-hydroxyindoline, 1-methyl-4-hydroxyindoline, 1-methyl-6-hydroxyindoline, 2-methyl-6-hydroxyindoline, 5-hydroxyindoline, 4-hydroxyindoline, 5,6-dihydroxyindoline and their respective salts.

Suitable coupling agents are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. 5-amino-2-methylphenol, 2-methyl-5-hydroxyethylaminophenol, 2,4-diamnophenoxyethanol, 2-amino-4-hydroxyethylaminoanisol, 2-methyl-5-amino-6-chlorophenol, 1,3-bis(2,4-diaminophenoxy)propane, 2-bis (2-hydroxyethyl)aminotoluene, 2-amino-5-methylphenol or the water-soluble salts thereof.

Concentration of one or more oxidative dyes in total—total concentration of precursors and couplers, if present—is in the range of 0.001 to 10% by weight, preferably 0.01 to 7.5% more preferably 0.05 to 5%, most preferably 0.1 to 3% by weight calculated to the total composition.

The emulsion composition can comprise one or more alkalizing agent. Suitable are sodium or potassium hydroxide, ammonia, alkanol amines such as monoethanolamine, carbonates such as ammonium carbonate, potassium carbonate, ammonium bicarbonate and ammonium chloride. Concentration of one or more alkalizing agents in total is in the range of 1 to 10% by weight calculated to the total composition. The most preferred are ammonia and monoethanolamine.

pH of the emulsion composition varies in the range of 6 to 10.5, preferably 6.5 to 10 when oxidative dye precursor are comprised in the composition. In case only direct dyes are comprised pH may suitably be in the range of 2 to 11.

Further, the emulsion compositions may comprise additional cationic polymer. Basically suitable are all cationic polymers listed under the generic name "Polyquaternium" in the CTFA International Cosmetic Ingredient Dictionary. Examples are Polyquaternium 6, Polyquaternium 7, Polyquaternium 10, Polyquaternium 11, Polyquaternium 22 and Polyquaternium 28, Polyquaternium 39, Polyquaternium 16 and Polyquaternium 87.

The cationic polymers also include the quaternized products of graft polymers from organopolysiloxanes and polyethyl oxazolines described in EP-A 524 612 and EP-A 640 643. Such polymer is known with its CTFA name Polysilicone-9.

Concentration of one or more additional cationic polymers is in the range from 0.05% to 2.5%, preferably 0.1% to 1.5% by weight, calculated to the total composition.

Further the above mentioned composition may comprise one or more organic solvent. Suitable organic solvents are 2-methyl-1,3-propanediol, mono and dialcohols or the ethers thereof, in particular mono-$C_1$-$C_3$-alkyl ether, ethanol, n-propanol, isopropyl alcohol, 1-methoxypropanol, 1-ethoxypropanol and ethoxydiglycol, diols and their esters 1,3- and 1,4-butanediol, diethyleneglycol and the monomethyl and monoethyl ether thereof, dipropylene glycol and the monomethyl and monoethyl ether thereof, glycerol, hexanetriol, ethyl carbitol, benzyl alcohol, benzyloxy ethanol, propylene carbonate, N-alkyl pyrrolidone, and urea or their mixture preferably in an amount from about 0.1% to 10% by weight, calculated to the total composition.

The above mentioned compositions can comprise further ceramide type of compound such as cetyl-PG-hydroxyethylpalmitamide.

Further optional ingredient are sterols, especially the phytosterols are useful hair restructuring compounds can be present in the above mentioned compositions. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

In a further preferred embodiment of the present invention, compositions may comprises at least one diamine compound. Preferred diamide compounds are according to the general structure

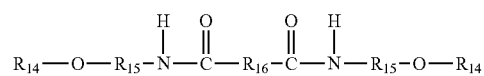

wherein $R_{14}$ is a linear or branched, saturated or unsaturated alkyl chain with 1 to 12 C atoms which may be substituted with hydroxy and/or alkoxy groups, preferably $R_{14}$ is linear or branched, saturated or unsaturated alkyl chain with 1 to 12 C atoms which may be substituted by 1 to 3 substituents selected from a hydroxy group and C1 to C6 alkoxy group, more preferably $R_{14}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{15}$ is linear or branched alkyl chain with 1 to 5 C atoms, preferably linear or branched alkyl chain with 2 to 5 C atoms and more preferably an alkyl chain with 2 to 3 C atoms, and $R_{16}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

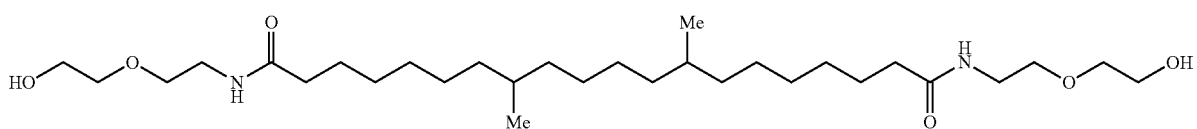

(A)

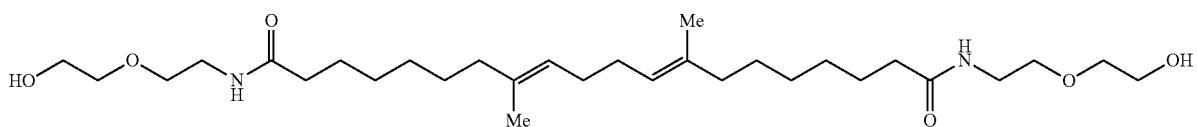

(B)

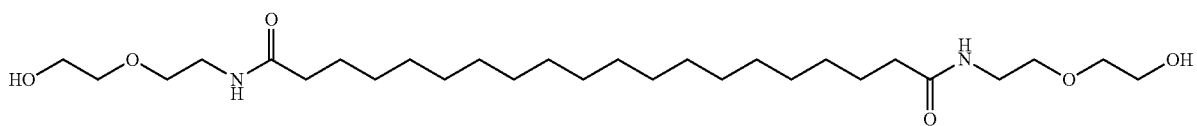

(C)

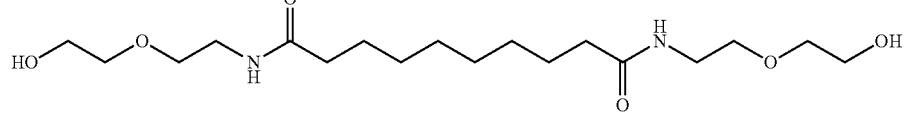

(D)

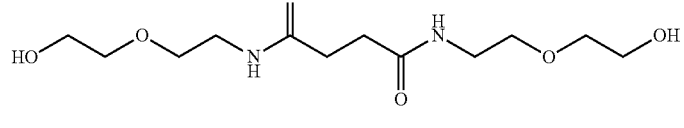

(E)

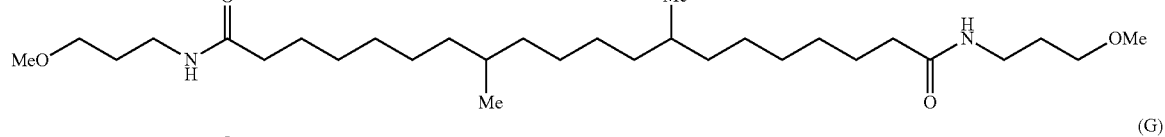

(F)

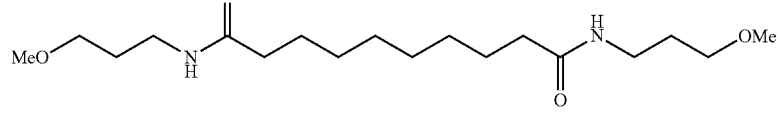

(G)

Particularly preferred diamide compound is the compound F which is bis(methoxypropylamido) isodocosane and commercially available from Kao Corporation—Japan.

Concentration of diamide compounds in the intermediate treatment compositions of the present invention is in the range of 0.001 to 5%, preferably 0.002 to 3% more preferably 0.005 to 2% and most preferably 0.01 to 1% by weight calculated to the total composition.

Further additional compounds may be present in the above mentioned compositions of the present invention is ubiqinone of the formula

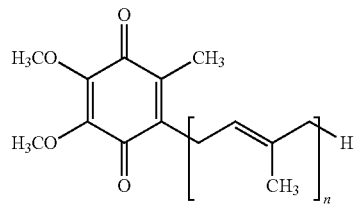

where n is a number between 1 and 10. Preferred ubiqinones are the ones where n is a number between 6 and 10 and especially preferred is Ubqhinone 50 where n is 10, also known as Coenzyme Q10. Concentration ubiqinone of the above formula in the compositions is from 0.0001 to 1%, preferably from 0.0002 to 0.75%, more preferably from 0.0002 to 0.5% and most preferably from 0.0005 to 0.5% by weight, calculated to the total composition.

The following examples are to illustrate but not to limit the invention.

EXAMPLE 1

Oxidizing Emulsion Composition

|  | % by weight |
|---|---|
| Cetearyl alcohol | 2.0 |
| Mineral oil | 2.5 |
| Sodium lauryl sulphate | 0.2 |

-continued

| | % by weight |
|---|---|
| Glycerin | 0.9 |
| Hydrogen peroxide | 9.0 |
| Salicylic acid | 0.05 |
| Etidronic acid | 0.2 |
| Phosphoric acid/sodium phosphate | 0.3 |
| Water | to 100 |

The above composition was produced in accordance with the claim 1 of the present specification. Namely, 40% of water, cetyl alcohol, mineral oil, glycerin, phosphoric acid and salicylic acid were mixed in a vessel at approximately 70° C. and after melting and dispersing the oil phase in water, sodium lauryl sulphate was added directly into the vessel and the composition was mixed until all surfactant was dissolved in the mixture. Afterwards, additional 40% of the water was added to the composition and therewith cooling of the batch was achieved. Under continuous mixing hydrogen peroxide was added and the remaining water was mixed to the composition. pH of the composition was measured at ambient temperature to be 2.1.

Volume size distribution of the emulsion thus obtained was analyzed using Sequip laser in situ particle size analyzer suitable for analysis particle in the range of 0.5 and 200 μm. The equipment is commercially available under the brand Sequip from Sequip S&E GmbH in Düsseldorf-Germany. It was found that the emulsion comprises only droplets smaller than 5 μm and has a very narrow size distribution range.

For comparative purposes, the above composition was produced according to the conventional method wherein all components including the surfactants were mixed at around 70° C. and the batch cooled down to ambient temperature. The pH of the composition was measured to be 2.1. It was observed that the composition had only turbid appearance and droplet size analysis showed that all droplets are larger than 20 μm.

The following examples are within the scope of the claims of the present invention.

EXAMPLE 2

Oxidizing Emulsion Composition

| | % by weight |
|---|---|
| Cetearyl alcohol | 2.0 |
| Almond oil | 2.5 |
| Cetrimonium Chloride | 0.2 |
| Glycerin | 0.9 |
| Hydrogen peroxide | 9.0 |
| Salicylic acid | 0.05 |
| Etidronic acid | 0.2 |
| Phosphoric acid/sodium phosphate | 0.3 |
| Water | to 100 | pH of the composition was measured at ambient temperature to be 2.1.

EXAMPLE 3

Oxidizing Emulsion Composition

| | % by weight |
|---|---|
| Myristyl Alcohol | 2.0 |
| Mineral oil | 2.5 |
| Ceteareth-30 | 1.0 |
| Glycerin | 0.9 |
| Hydrogen peroxide | 9.0 |
| Salicylic acid | 0.05 |
| Etidronic acid | 0.2 |
| Phosphoric acid/sodium phosphate | 0.3 |
| Water | to 100 | pH of the composition was measured at ambient temperature to be 2.1.

EXAMPLE 4

Oxidizing Emulsion Composition

| | % by weight |
|---|---|
| Behenyl Alcohol | 2.0 |
| Cetyl Palmitate | 2.5 |
| Sodium lauroyl glutamate | 1.0 |
| Glycerin | 0.9 |
| Hydrogen peroxide | 9.0 |
| Salicylic acid | 0.05 |
| Etidronic acid | 0.2 |
| Phosphoric acid/sodium phosphate | 0.3 |
| Water | to 100 | pH of the composition was measured at ambient temperature to be 2.1.

EXAMPLE 5

Emulsion Composition

| | % by weight |
|---|---|
| Cetearyl alcohol | 2.0 |
| Mineral oil | 2.5 |
| Sodium lauryl sulphate | 0.2 |
| Glycerin | 0.9 |
| Salicylic acid | 0.05 |
| Phosphoric acid/sodium phosphate | 0.2 |
| Water | to 100 | pH of the composition was measured at ambient temperature to be 6.5.

The invention claimed is:

1. A method of producing an emulsion composition, said composition comprising one or more fatty alcohol, one or more oil which is liquid at 20° C., and one or more surfactant, said method comprising:
 adding one or more surfactant to a dispersion of the one or more fatty alcohol and the one or more oil liquid at 20° C. in water at a temperature of 50° C. or higher, with the condition that the temperature of the dispersion is at least 10° C. higher than melting point of the one or more fatty alcohol, thus forming an emulsion, wherein the emulsion does not comprise dispersed droplets with a volume size of larger than or equal to 10 μm measured directly without dilution of the emulsion at 20° C., and measured with a laser particle size analyzer suitable therefore.

2. The method according to claim 1, wherein the one or more fatty alcohol is selected from fatty alcohols of the general structure $$R_1—OH$$

wherein $R_1$ is a saturated or unsaturated, straight or branched alkyl chain having 12 to 30 C atoms which may also be substituted with one or more OH groups.

3. The method according to claim 1, wherein the one or more oil is selected from synthetic oil and natural oil.

4. The method according to claim 1, wherein weight ratio of the one or more fatty alcohol to the one or more oil is less than or equal to 1.

5. The method according to claim 1, wherein the emulsion comprises mineral oil which is liquid at 20° C.

6. The method according to claim 1, wherein the one or more surfactant is selected from anionic, nonionic and cationic surfactant.

7. The method according to claim 1, wherein the one or more surfactant is anionic.

8. The method according to claim 1, wherein the one or more surfactant is selected from cationic surfactants according to general structure $$R_9—\overset{\overset{R_8}{|}}{\underset{\underset{R_{11}}{|}}{N^+}}—R_{10} \quad X^-$$

where $R_8$ is a saturated or unsaturated, branched or non-branched alkyl chain with 8-22 C atoms, or $$R_{12}CO\ NH(CH_2)_n$$

where $R_{12}$ is saturated or unsaturated, branched or non-branched alkyl chain with 7-21 C atoms and n has typical value of 1-4, or $$R_{13}CO\ O(CH_2)_n$$

where $R_{13}$ is saturated or unsaturated, branched or non-branched alkyl chain with 7-21 C atoms and n has typical value of 1-4, and and $R_9$, $R_{10}$ and $R_{11}$ are independent from each other H or lower alkyl chain with 1 to 4 carbon atoms, and X is an anion.

9. The method according to claim 1, wherein weight ratio of the one or more surfactant to total of the one or more fatty alcohol and the one or more oil is less than or equal to 0.25.

10. The method according to claim 1, wherein the emulsion comprises at least one oxidizing agent.

11. The method according to claim 1, wherein the emulsion comprises one or more of the compounds selected from
a-Cationic polymer,
b-Organic solvent,
c-Ceramide,
d-Phytosterol,
e-Diamide compound according to general structure $$R_{14}—O—R_{15}-\overset{\overset{H}{|}}{N}—\overset{\overset{O}{\|}}{C}—R_{16}-\overset{\overset{O}{\|}}{C}—\overset{\overset{H}{|}}{N}—R_{15}-O—R_{14}$$

wherein $R_{14}$ is a linear or branched, saturated or unsaturated alkyl chain with 1 to 12 C atoms which may be substituted with hydroxy and/or alkoxy groups, $R_{15}$ is linear or branched alkyl chain with 1 to 5 C atoms, and $R_{16}$ linear or branched, saturated or unsaturated alkyl chain with 1 to 22 C atoms, and f-Ubiqinone according to general structure

[chemical structure of ubiquinone with $H_3CO$ groups, $CH_3$ groups, and isoprenoid side chain with subscript $n$]

where n is a number between 1 and 10.

12. A process for treating hair, comprising:
(a) mixing the composition manufactured according to the method of claim 1 with a second composition, and
(b) applying onto hair a mixture obtained from step (a), and
(c) leaving the mixture obtained from step (a) on hair for a period 1 to 45 min, and
(d) rinsing the mixture obtained from step (a) off from hair.

13. The process according to claim 12, wherein the second composition comprises at least one hair dye.

14. A kit comprising two or more compositions, wherein one of the two or more compositions is an emulsion manufactured in accordance with the method of claim 1.

15. The method according to claim 1, wherein the temperature of the dispersion is 60° C. or higher.

16. The method according to claim 2, wherein the one or more fatty alcohol is present at a concentration in the range of 1 to 20% by weight calculated to the total of the composition.

17. The method according to claim 2, wherein the one or more fatty alcohol is solid at 20° C.

18. The method according to claim 3, wherein the one or more oil is present at a concentration in the range of 1 to 20% by weight calculated to the total of the composition.

19. The method according to claim 6, wherein the one or more surfactant is present at a total concentration of 0.05 to 10% by weight calculated to the total of the composition.

20. The method according to claim 7, wherein the one or more surfactant is sodium lauryl sulfate.

* * * * *